(12) United States Patent
Power (10) Patent No.: US 8,294,897 B2
(45) Date of Patent: Oct. 23, 2012

(54) METHOD FOR IMAGING A SAMPLE USING A MICROSCOPE, AND MICROSCOPE AND DATA STORAGE CENTER

(75) Inventor: Christopher Power, Jena (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 188 days.

(21) Appl. No.: 12/576,596

(22) Filed: Oct. 9, 2009

(65) Prior Publication Data
US 2010/0091287 A1 Apr. 15, 2010

(30) Foreign Application Priority Data
Oct. 10, 2008 (EP) .................................. 08017814

(51) Int. Cl.
*G01N 21/25* (2006.01)
(52) U.S. Cl. ............. 356/417; 356/634; 359/385
(58) Field of Classification Search ................. 356/417, 356/634; 359/385
See application file for complete search history.

(56) References Cited

U.S. PATENT DOCUMENTS

| | | | |
|---|---|---|---|
| 6,300,639 B1 | 10/2001 | Wiederhoeft | |
| 7,218,762 B2 | 5/2007 | Olschewski | |
| 7,257,289 B2 | 8/2007 | Olschewski | |
| 7,280,203 B2 | 10/2007 | Olschewski | |
| 7,365,842 B2 | 4/2008 | Kitagawa | |
| 7,554,664 B2 * | 6/2009 | Wolleschensky et al. | .... 356/417 |
| 7,593,158 B2 | 9/2009 | Wilhelm et al. | |
| 2003/0179372 A1 | 9/2003 | Knebel | |
| 2003/0206341 A1 * | 11/2003 | Wolleschensky et al. | .... 359/385 |
| 2003/0231825 A1 | 12/2003 | Olschewski | |
| 2004/0209300 A1 | 10/2004 | Storz et al. | |
| 2005/0046835 A1 | 3/2005 | Olschewski | |
| 2006/0012874 A1 * | 1/2006 | Funk et al. | ................. 359/388 |
| 2007/0133086 A1 | 6/2007 | Wilhelm et al. | |
| 2008/0024782 A1 | 1/2008 | Wolleschensky et al. | |
| 2008/0062511 A1 * | 3/2008 | Wolleschensky | ............ 359/385 |

FOREIGN PATENT DOCUMENTS

DE 198 35 070 2/2000
(Continued)

OTHER PUBLICATIONS

European Opposition to EP 2175301 dated Mar. 2, 2011.
(Continued)

*Primary Examiner* — Tarifur Chowdhury
*Assistant Examiner* — Isiaka Akanbi
(74) *Attorney, Agent, or Firm* — Frommer Lawrence & Haug LLP (57) ABSTRACT

The invention relates to a method for imaging a sample using a microscope, in particular a scanning microscope, in which the sample is illuminated with excitation light via an illuminating beam path, and light emitted from the sample is recorded via a detection beam path, wherein at least one adjustable beam splitter having an adjustable threshold wavelength is arranged in the detection beam path or/and in the illuminating beam path, and wherein light emitted from the sample is detected in at least one detection channel. According to the inventive method, for at least one predetermined sample region, a signal intensity of light detected in the at least one detection channel is recorded for a plurality of threshold wavelengths set at the adjustable beam splitter to obtain a signal/threshold-dependency of the predetermined sample region.

21 Claims, 8 Drawing Sheets

FOREIGN PATENT DOCUMENTS

| | | |
|---|---|---|
| DE | 10038526 | 2/2002 |
| DE | 10227111 | 12/2003 |
| DE | 10319946 | 11/2004 |
| DE | 10 2004 029733 | 2/2005 |
| DE | 102004029733 | 2/2005 |
| DE | 10339312 | 3/2005 |
| EP | 1795938 | 6/2007 |
| EP | 1 882 969 | 1/2008 |
| EP | 1882969 | 1/2008 |
| JP | 2006-039116 | 2/2006 |
| WO | WO 02/01222 | 1/2002 |

OTHER PUBLICATIONS

R. Borlinghaus: "Colours Count: how the Challenge of Fluorescence was solved in Confocal Microscopy", A. Méndez-Vilas and J. Diaz [Eds.]: "Modern Research and Educational Topics in Microscopy", Formatex, 2007.

R. Borlinghaus et al.: "Closing the spectral gap—the transition from fixed-parameter fluorescence to tunable devices in confocal microscopy", Proc. of SPIE vol. 6090, 2006.

Leica TCS SPS/TCS SP5 X Betriebsanleitung[Use Manual], Leica Microsystems CMS GmbH, Feb. 2008.

J. Rietdorf und E.H.K. Stelzer, "Special Optical Elements", Chapter 2, pages 43ff, 2006.

P.-C. Cheng, "The Contrast Formation in Optical Microscopy", Chapter 8, pp. 162ff, 2006.

J. B. Pawley, "Light Paths of the Current Commercial Confocal Light Microscopes Used in Biology", Appendix 2, pp. 906 ff, 2006.

J. B. Pawley, "Handbook of Biological Confocal Microscopy" Springer, 2006.

Installation Test Protocol TCS SP5 x (ITP)—E2b—Leica Microsystems GmbH, Germany S/N: 5100000577 Apr. 9, 2008 2007—pp. 1-7.

E2a—Central Procurement Sect. 4.1—Ruprecht-Karls University Heidelberg Aug. 23, 2007.

* cited by examiner

METHOD FOR IMAGING A SAMPLE USING A MICROSCOPE, AND MICROSCOPE AND DATA STORAGE CENTER

The present application claims priority from European Patent Application No. EP 08017814.8-2217 filed on Oct. 10, 2008, the disclosure of which is incorporated herein by reference in its entirety.

BACKGROUND OF THE INVENTION

1. Field of the Invention

The invention relates to a method for imaging a sample using a scanning microscope. In such a method, the sample is illuminated with excitation light via an illuminating beam path, and light emitted from the sample is recorded via a detection beam path, wherein at least one adjustable beam splitter having an adjustable threshold wavelength, in particular a gradient filter, is arranged in the detection beam path or/and in the illuminating beam path, and wherein light emitted from the sample is detected in at least one detection channel.

In further aspects, the invention relates to a scanning microscope and a data storage carrier on which a program for driving a control unit of a scanning microscope is stored.

2. Description of Related Art

EP 1 882 969 A1 and US 2008/0024782 A1 disclose a laser scanning microscope having at least one gradient filter spatially variable in regard to the threshold wavelength between transmission and reflection, which is provided in the detection beam path for the selection of the detection-wavelengths. This filter type allows to easily change the spectral set-up of the microscope when the sampling conditions change, so that a highly versatile microscope is obtained.

DE 10 2004 029 733 A1 discloses a scanning microscope having a band-pass filter in the detection beam path, which band-pass filter comprises a combination of a low-pass filter and a high-pass filter. Said low-pass filter and said high-pass filter can be spectral gradient filters.

US 2008/0062511 A1 discloses a laser scanning microscope with a narrow angle main beam splitter.

SUMMARY OF THE INVENTION

It is an objective of the invention to provide a new form of spectral acquisition that, particular with low loss of light, allows to gather unique and meaningful spectroscopic data accurately, flexibly, and easily.

This objective is solved with a method for imaging a sample including an illumination step, in which a sample is illuminated with excitation light via an illuminating beam path, and a recording step, in which light emitted from the sample is recorded via a detection beam path. In this method, at least one adjustable beam splitter having an adjustable threshold wavelength is arranged in the detection beam path or/and in the illuminating beam path, and light emitted from the sample is detected in at least one detection channel.

The inventive method is characterized in that, for at least one predetermined sample region, a signal intensity of light detected in the at least one detection channel is recorded for a plurality of threshold wavelengths set at the adjustable beam splitter. Thereafter, a signal/threshold-dependency of the predetermined sample region is obtained based on the signal intensity of light detected.

A fundamental idea of the invention resides in the fact that at least one variable beam splitter having a variable threshold wavelength (i.e., cut off wavelength) is placed in the scanning beam path of an optical scanning microscope, and that for at least one imaging location, the threshold wavelength setting of the beam splitter is changed so that for said location, a dependency of the detected signal intensity versus threshold wavelength (i.e., a signal intensity/threshold wavelength-dependency or, in short, a signal/threshold-dependency) is acquired. The signal intensity/threshold wavelength-dependency, which could also be named "Differential Lambda Stack" (DLS), is acquired by varying the spectrum of the excitation and/or by varying the detected part of the spectrum and monitoring the change in signal in the detection channel or channels. Thus, according to the invention, a variable form of spectral division is used on the excitation and/or on the detection side.

The inventive form of spectral acquisition allows a simple, reliable and cost effective collection of spectral information into one or more channels in such a way that very little if any sensitivity is lost. In a two or more channel system in which the beam splitter splits-off the individual channels, it is possible to loose no light in the splitting of the spectra and have a completely efficient system. For example, in the case of an emission DLS on a two-channel system, as the threshold wavelength is moved across the spectrum, the signal reduction in one channel should be matched by a corresponding increase in the other channel. In this way, unless additional filters are used in the channels, the light always goes to one of the two channels and is never lost.

It is generally preferred to use a scanning microscope, in particular a confocal scanning microscope, for carrying out the inventive method. The confocal microscope can, for example, be a single photon or a multi photon laser scanning microscope. Although laser scanning microscopes are generally preferred, the inventive method can also be carried out in advantageous manner using a widefield microscope where the whole field of view is imaged simultaneously and no scanning is necessary. In this case, bigger beam splitters might preferably be used to take into account the bigger beam diameters with widefield microscopes.

According to the invention, the threshold wavelength change can be applied to the emission light (i.e., the detection beam path) or to the excitation light (i.e., the illuminating beam path). The latter could be particularly useful with white light sources. A threshold wavelength change could also be applied to both emission and excitation light, resulting in "Lambda squared stacks".

The inventive microscope is an optical microscope, in particular a scanning microscope and preferably a confocal scanning microscope. The sample is preferably illuminated by laser light via the illuminating beam path. The measured detector signal is preferably correlated to the light intensity present in the detection channel. The inventive detection channel is located at the detection beam path.

The adjustable beam splitter can particularly be a dichroic element and can be a long pass filter or a short pass filter. The threshold wavelength can be considered to be the wavelength at which transmission sets in, especially the wavelength between transmission and reflection. Preferably, the adjustable beam splitter is a color gradient filter, on which the threshold wavelength for transmission varies in dependence of the position on the filter, so that, for example, the threshold for transmission is 500 nm at one place and 600 nm at another place of the filter surface.

Preferably, the microscope comprises a control device for setting the adjustable beam splitter. The change of threshold wavelength can then be automated, especially by software. If a gradient filter is provided, the control device can be provided with an actuator for moving the gradient filter in space for setting the threshold wavelength. However, in principle, the setting of the adjustable filter could also be performed non-automatically (i.e., live by the user) to get a visual impression of the spectral split (i.e., by moving a slider whilst scanning).

According to another inventive aspect, at least one fluorochrome on or in the sample is excited by the excitation light and emission light is emitted by the fluorochrome. For obtaining the signal/threshold-dependency, the adjustable beam splitter is then set to a plurality of threshold wavelengths in a wavelength region where emission light of the fluorochrome occurs. By setting the threshold wavelengths in the vicinity of an emission structure of the fluorochrome, it is possible to gather information on the spectral shape of the emission structure. In typical cases there are two or more fluorochromes on or in the sample. In this case, choosing threshold wavelengths in the vicinity of spectral emission structures of the fluorochromes permits to acquire information on the spectral overlap of the emission structures of different fluorochromes (i.e., on the bleed-through).

According to the present description, the term fluorochrome should be understood in a broad sense. A fluorochrome could be a fluorophore, a fluorescent dye, a fluorescent protein, a non biological fluorescing tag (e.g., quantum dots) or any substance which yields a known and reasonably predictable fluorescence response when exposed to light. Even though not fluorescent, other predictable spectral responses like reflection, harmonics (e.g., Second Harmonics Generation and Third Harmonics Generation) two-photon-effects, and absorption should be treated the same as fluorochromes for all purposes of this disclosure.

Whilst a solution having only one detection channel can be preferable in terms of costs, another preferred embodiment of the invention is characterized in that by means of the adjustable beam splitter, the detection beam path is split into two detection channels, and a signal/threshold-dependency is recorded for each of the two detection channels. This embodiment is particularly advantageous with respect to sensitivity. In a two channel system it is possible to prevent losses of light, since the spectrum filtered out from one channel is reflected into the other channel and vice versa. As a result, the signal reduction in one channel should generally be matched by a corresponding increased in the other channel. Preferentially, the signal/threshold-dependencies of both channels are evaluated in common. Collecting both the transmitted light of the beam splitter in one channel and the reflected light of the beam splitter in another channel furthermore permits additional data processing techniques, which will be described further below.

For even more advanced spectroscopic techniques, it is possible to have more than one beam splitter in the detection beam path, so that the two detection channels are further divided into sub-channels, resulting in three or more detection channels.

For some applications, it might be sufficient to record a signal/threshold-dependency only for a single sample region. However, according to a preferred embodiment of the invention, signal/threshold-dependencies are recorded at a plurality of predetermined sample regions. The individual dependencies can then be evaluated individually, or they can also be averaged before further processing is carried out. By recording the dependencies at the plurality of predetermined sample regions, it is possible to obtain spatially resolved signal/threshold-dependencies. Preferentially, signal/threshold-dependencies are recorded for all pixels of a scan (i.e., for all sample regions successively imaged during scanning).

When signal/threshold-dependencies are to be recorded at a plurality of predetermined sample regions, it is possible to go through all desired threshold wavelengths whilst the measured sample region is kept fixed at a first location, to subsequently shift the measured sample region to a second location, to then go through all desired threshold wavelengths again for this second location, to then shift to a third location and so forth. Alternatively, it is possible to keep the threshold wavelength fixed to a first value and to acquire the signal intensity with this setting for all sample regions of interest, to then set the threshold wavelength to a second threshold value and to gather the signal intensity for all the sample regions of interest with this second value and so forth. If scanning of the sample can be performed faster when compared with the setting of the adjustable beam splitter, the latter operating mode is usually preferred.

Thus, according to a preferred embodiment of the invention, the threshold wavelength set at the adjustable beam splitter is changed once a pixel, a line, a frame or a z-stack has been scanned. Changing the wavelength at the beam splitter once a frame has been scanned is preferred if setting of the splitter is slow when compared with scan speed.

In case there are two fluorochromes with overlapping emission spectra present, there exists a spectral point where the emission lines of the two fluorochromes show comparable intensities. This spectral point would therefore be the best point to set a spectral division means like the adjustable beam splitter in order to acquire the spectral emissions for both fluorochromes whilst reducing the effort required for subsequent unmixing of scanned images. If the overlap between the emission spectra of the two fluorochromes is small, unmixing might even become dispensable if the spectral division means is set at this wavelength during scanning. This best point in the spectrum can be determined from the acquired signal/threshold-dependencies. Therefore, according to another preferred embodiment of the invention, from the signal/threshold-dependency or dependencies, at least one setting wavelength is determined, the setting wavelength representing the best setup of a spectral division means, particularly of the adjustable beam splitter, for resolving or distinguishing fluorochromes with overlapping emission spectra.

It is particularly preferred that the setting wavelength is determined by analyzing the slope of the signal/threshold-dependency or dependencies. From a signal/threshold-dependency, it is possible to create a graph in which the signal of each channel may rise or fall as the threshold wavelength increases. The shape of the graph will give information about the number of different fluorochromes in the sample and how much they overlap. For instance, in a falling graph, each fluorochrome can be seen as a region with a steeper gradient (dip). In contrast, each point with the largest separation between fluorochromes, that is each point best suited to set the spectral division, will be seen as a less steep curve (i.e., as a local minimum in the absolute value of the gradient (bump)). Thus, it is possible to analyze the signal/threshold-dependencies for wavelengths at which "bumps" in the curve occur, and assign these points to a setting wavelength.

According to another preferred embodiment of the invention, threshold wavelength-dependent scatter plots using the intensities of pixels in the two channels as its two axes are generated from the signal/threshold-dependencies. A scatter plot, which can also be called a fluorogram, is a statistical chart that visualizes the intensity distribution of image pixels in a pair of images, each image being taken in a different channel. The scatter plot uses intensities of pixels in each of the two channels (i.e., in each of the two images) as its two axes. Each pixel will be located in the plot according to its intensities in both channels. If there is no bleed through between the channels, two fluorochromes will give two lines on or very close to the axes of the scatter plot. However, if there is bleed through between two of the detection channels, for a given intensity in one channel a fluorochrome also has a detectable presence in the other channel. This is visible in the scatter plot as a deviation from the plot axes. Therefore, scatter plots are traditionally used as a way of analyzing spectral bleed through between combinations of dyes in a fluorescent image. In particular, scatter plots are used for co-localization analysis and to check for deviations of the pure fluorochrome components from the graph axes. Traditionally, this is performed offline and for a fixed optical configuration.

However, when, according to the invention, signal/threshold-dependencies are acquired, it is also possible to produce threshold wavelength-dependent scatter plots. These threshold wavelength-dependent scatter plots can be produced live and monitored as the beam splitter is tuned. The inventive wavelength-dependent scatter plots can be used to look for the wavelength at which an area between lines which are assigned to the outermost pixels (i.e., the pixels closest to the axis) corresponding to the first and the second fluorochrome, respectively, is at maximum, implying that the bleed through is at minimum. The wavelength at which this occurs could be assigned to the above-mentioned setting wavelength.

Therefore, another preferred embodiment of the invention is characterized in that the setting wavelength is determined by analyzing the wavelength-dependent scatter plots.

Alternatively or additionally, one could plot the area between the two fluorochromes particularly between the lines given by the outermost pixels related to these fluorochromes, as this is relative to the degree of separation between the two fluorochromes. This would also allow the user to assess if the widening of the angle between the lines makes up for the drop in signal when additional emission filters are used to further reduce bleed through between the two channels.

Traditional scatter plots typically calibrate the x-axis and y-axis in terms of signal grey level. If the inventive system is well calibrated, it would also be possible to plot these axes in terms of real photons per pixel.

It is further preferred that, subsequent to the determination of the setting wavelength, the adjustable beam splitter is set to the setting wavelength, and subsequently, with a fixed setting of the beam splitter at the setting wavelength, the sample or another sample is imaged. According to this embodiment, the best setting of the beam splitter for imaging overlapping fluorochromes is determined in a first step on the basis of signal/threshold-dependency data, and in the following step, this setting is used for imaging the same or another sample. This imaging method provides for a particularly fast imaging. In particular, it is possible to acquire a signal/threshold-dependency of a typical sample to obtain the setting wavelength and to use this wavelength for similar samples without having to acquire another signal/threshold-dependency.

Said embodiment makes use of the fact that, particularly if the signal-to-noise ratio of the returning signal is good, it might be sufficient for imaging to simply acquire a limited subset of images and then perform channel unmixing on them if required. In a simple case of a two channel detection system with two fluorochromes, there will be an optimal position of the beam splitter, namely the above-mentioned setting wavelength, in order to acquire sufficient information to obtain high quality images after unmixing. Therefore, instead of acquiring signal/threshold-dependencies at all sample locations, it might be preferable to choose a fixed wavelength to divide the light at the beam splitter, then just acquire a single image in each channel and then perform channel unmixing on the obtained data. To determine the setting wavelength of the beam splitter, one could acquire the signal/threshold-dependency of a typical sample. The microscope could then automatically produce paired unmixed images in dependence of the threshold wavelength. The user can then see which wavelength gives the best result without having to acquire signal/threshold-dependencies of the following samples. This method is particularly suitable if the sample is moving or prone to photobleaching since it allows fast imaging without having to acquire a large number of images, resulting in short total illumination times.

Moreover, according to the invention, it is preferred that from the signal/threshold-dependency or dependencies, at least one spectrum of emission light emitted from the sample versus the wavelength of the emission light is calculated, in particular by differentiating the signal/threshold-dependency or dependencies. According to this embodiment, the obtained signal/threshold-dependencies are converted to "traditional" emission spectra, which show the signal strength versus wavelength or frequency. A "traditional" spectrum of emission light can be calculated stepwise form the signal/threshold-dependency.

If signal/threshold-dependencies have been taken at multiple sample regions, in particular for all pixels, the back calculation to obtain a "traditional" spectrum can be applied to all spatially separated dependencies. So, by applying the back calculation technique to the actual image, one could create a back calculated spectral series that would have the appearance of a spectral series collected on a "traditional" instrument.

The raw spectra determined from the raw signal/threshold-dependencies can be used as input data for a spectral unmixing step. Such an unmixing step involves the determining of the levels of bleed through between the emission structures in a mathematical processing step to reassign the spectral bleed through to the correct emission structure.

Thus, the back calculated spectra can be used as reference spectra for the unmixing of the pure fluorochromes from the back calculated spectral series images.

According to another preferred embodiment of the invention, there is at least one additional filter in the detection beam path and/or in the illuminating beam path, particularly in order to increase performance of a detector located in the detection channel in a threshold wavelength region to be studied. The performance to be increased is preferably a dynamic range of the detector. By using such a filter, detector overload due to emission light in spectral regions not of interest can be prevented through suppression of the unwanted spectral contributions. The additional filter could be a long-pass, a short-pass or a band-pass filter. The filter can, for example, be located immediately in front of the detector in order to restrict the spectral range detected. The inclusion or exclusion and/or the changing of filters during the acquisition of the signal/threshold-dependency can increase the dynamic range of the dependency, which might allow the detection of higher numbers of fluorochromes and/or the detection of fluorochromes with significantly different signal levels.

According to another preferred embodiment of the invention, each of the two detection channels is provided with at least one detector, and for setting up the range of the detectors, particularly the dynamic range of the detectors, the threshold wavelength of the adjustable beam splitter is set to a first extreme wavelength so that the intensity at a first detector is at maximum, and then the range of the first detector is set. By preference, subsequently the threshold wavelength of the adjustable beam splitter is set to a second extreme wavelength so that the intensity at a second detector is at maximum, and then the range of the second detector is set. This embodiment allows for particularly easy, fast and reliable setting of the range of the two detectors. In particular, it is possible to set up the dynamic range for the whole spectral series in just two scans. The embodiment makes use of the fact that in a two channel setup, all the light is divided between the two channels. According to the embodiment, the beam splitter is first moved to one extreme so that all of the light is diverted to the first channel. Then, the first channel is calibrated to ensure the dynamic range is filled but not saturated. Afterwards, the beam splitter is moved to the other extreme so that all of the light enters the other detector. Then the other detector is calibrated to ensure that the dynamic range of the other detector is also filled but not saturated.

In some circumstances, it is even possible to omit the second calibration step (i.e., to omit setting the threshold wavelength of the beam splitter to a second extreme wavelength for setting the range of the second detector). This is in particular possible if the detector response (e.g., gain response) is well calibrated between the two detectors, so that calibration of one detector can be applied to the other detector. In this case, detector calibration could even be performed in one scan, thus further reducing the number of required previous series to set the range. This is particularly useful if the sample is prone to photobleaching.

Due to the nature of the inventive data acquisition, the signal will rise in one detector and, if present, fall in the other detector when the threshold wavelength of the adjustable beam splitter is either steadily raised or steadily lowered during data acquisition. If the detector response (i.e., gain response, exposure time, and so forth) is known, it is possible to increase or decrease the sensitivity of the detector for each spectral step in order to adapt the dynamic range as the series is performed. Therefore, according to another preferred embodiment of the invention, particularly based on information of the detector response, detector sensitivity of at least one detector of the detection beam path is changed as the threshold wavelength of the adjustable beam splitter is changed.

Moreover, it is preferable according to the invention that the threshold wavelength which is set at the adjustable beam splitter is changed in steps, and the size of the steps is changed in dependency of the current threshold wavelength. In particular, it is possible to decrease the size of the steps in a wavelength region where emission light of the at least one fluorochrome occurs and/or were the signal gradient in the signal/threshold-dependency is steep. Alternatively or additionally, the step size could be increased when the ratio shift between the two channels is small and decreased when the ratio shift between the two channels is larger. In this way, a higher signal to noise ratio can be obtained and it is possible to differentiate between closely overlapping spectra.

It is therefore particularly preferable that the size of the steps is changed based on information obtained from a graphical representation of a signal/threshold-dependency. Preferably, the size of the steps is chosen such that the density of the steps per wavelength interval increases with the absolute value of the slope of the graphical representation of the signal/threshold-dependency.

In another preferred embodiment, the signal/threshold-dependency used for determining the size of the steps is acquired by a measurement with reduced intensity of excitation light. According to this embodiment, the data acquisition used for determining the step size, which is usually carried out before the actual imaging takes place, is performed with lower intensity as compared with the actual imaging. This is particularly advantageous if there is a risk of photobleaching.

In fluorescence microscopy, the signal strength of the light emitted from the sample is of great interest. A useful metric for measuring the signal strength is the number of detected photons per pixel (PPP). However, when determining photons per pixel, there is a problem that shot noise limits the accuracy of the measurement. Shot noise is proportional to the square root of the count. Therefore, if the photon per pixel count is for example 100, then the error is $\sqrt{100}=10$, which means that one might get any value between 90 and 110 as a result of shot noise.

In order to calculate the exact PPP value, it is ideally necessary to perform multiple measurements of the same pixel in order to determine an average. This aspect can be exploited in another preferred embodiment of the invention, since the inventive signal/threshold-measurements imply that the sample is scanned multiple times and that the same pixels are recorded multiple times. Therefore, evaluating these dependencies can be used to reduce shot noise.

However, when using the signal/wavelength-dependencies for determining signal strength, it has to be considered that the beam splitter splits the total signal strength (i.e., the value of interest, between the channels). Therefore, to obtain a measure which represents total signal strength, it is preferred to add the signals of the individual channels together. Accordingly, a preferred embodiment of the inventive method is given in that by means of the at least one adjustable beam splitter, the detection beam path is split into a plurality of detection channels, a signal/threshold-dependency is recorded for each of the detection channels, from the signal/wavelength-dependencies of all channels, the signal values present at a common threshold wavelength are extracted, the signal values present at the common threshold wavelength are added to give a summed signal value at the common threshold wavelength, and the summed signal value is used as a measure of signal strength. For example, in a two channel system, since all light is always directed to one of the two channels, one should obtain a constant signal level, apart from the shot noise effects, if the signals are added together at various different common threshold wavelengths.

Moreover, it is preferred that summed signal values are determined for a plurality of common threshold wavelengths, and that the summed signal values are averaged to obtain a measure of signal strength with reduced relative shot noise. Preferably, the summed signal values are averaged over the whole signal/wavelength-dependency, which means that the summed signal values for all recorded threshold values are averaged. Due to this averaging process, the number of measurements available is increased, which reduces relative shot noise.

The effect of averaging summed signal values over the whole of the DLS (signal/wavelength-dependency) is shown in the following table 1. Table 1 shows the photon per pixel measurement improvement over a (theoretical) signal/wavelength-dependency series. In this example, a single fluorochrome with a strength of 100 photons per pixel is detected and a signal/wavelength-dependency is recorded at eleven steps (i.e., eleven wavelengths of the beam splitter). As the threshold-wavelength changes, the distribution of the signal between the two channels (PMT1 and PMT2) changes, and whilst the signal in one channel decreases, it increases in the other channel. In this example, a single scan would have a 10% error associate with it. If the average is taken over the whole dependency, the error can be reduced to just 3%, as shown in the last column of the table.

TABLE 1

| Wavelength of split | PMT1 | PMT2 | PPP | Error from shot noise | Error as percentage of signal | Cumulative PPP | Cumulative error from shot noise | Cumulatative Error as percentage |
|---|---|---|---|---|---|---|---|---|
| 500 | 100 | 0 | 100 | 10 | 10% | 100 | 10 | 10.0% |
| 510 | 90 | 10 | 100 | 10 | 10% | 200 | 14.14213562 | 7.1% |
| 520 | 80 | 20 | 100 | 10 | 10% | 300 | 17.32050808 | 5.8% |
| 530 | 70 | 30 | 100 | 10 | 10% | 400 | 20 | 5.0% |
| 540 | 60 | 40 | 100 | 10 | 10% | 500 | 22.36067977 | 4.5% |
| 550 | 50 | 50 | 100 | 10 | 10% | 600 | 24.49489743 | 4.1% |
| 560 | 40 | 60 | 100 | 10 | 10% | 700 | 26.45751311 | 3.8% |
| 570 | 30 | 70 | 100 | 10 | 10% | 800 | 28.28427125 | 3.5% |
| 580 | 20 | 80 | 100 | 10 | 10% | 900 | 30 | 3.3% |
| 590 | 10 | 90 | 100 | 10 | 10% | 1000 | 31.6227766 | 3.2% |
| 600 | 0 | 100 | 100 | 10 | 10% | 1100 | 33.1662479 | 3.0% |

In another preferred embodiment of the invention, a main beam splitter is provided for the spatial separation of the illuminating beam path and the detection beam path. Advantageously, the main beam splitter has a high optical density. By using a main beam splitter with sufficiently high optical density, further blocking of returning reflection light might become dispensable. It is particularly preferred to use a narrow angle main beam splitter. Using a main beam splitter with high optical density can help to remove potential constraints on the design of the spectral system. In particular there might be no need for additional components to add extra optical density, which components might introduce unwanted spectral effects on the acquired emission. This again allows the wavelengths of the excitation and of the emission collection to be defined relatively freely. Using a high optical density main beam splitter also means the dynamic range of detection is not compromised by the reflection.

The invention also involves a scanning microscope being configured to automatically carry out the inventive method. For this purpose, the scanning microscope is preferably provided with a control device (i.e., a controller) which is in operative connection with a setting device for setting the adjustable threshold of the beam splitter. When the adjustable beam splitter is a gradient filter with a spatially variable threshold wavelength, the setting device can for example be the actuator for moving the adjustable beam splitter in space. The control device can also be in operative connection with a light source which produces excitation light and/or with a scanner of the microscope. It can also be in signal connection with detectors provided in the detection channels. Preferably, the control device is configured to automatically carry out the inventive method.

The invention also relates to a data storage carrier and a computer program product, each comprising program code for carrying out the inventive method when the program is executed on a controller or a control unit of a scanning microscope.

The advantages of the invention can be summarized as follows:
1. With regard to fluorochrome characterisation:
   a. By performing sufficiently high laser suppression remote from the spectral system, and particularly at the main beam splitter, the spectral system is free and flexible in its positioning.
   b. The spectral step size and range covered can be very flexible in the inventive approach.
   c. The reproducibility is only limited by the mechanical accuracy of the component, particularly of the adjustable beam splitter and/or its actuator, and can therefore be very high.
2. With regard to spectral acquisition:
   a. A new 3$^{rd}$ form of spectral acquisition, the DLS acquisition (signal intensity versus threshold wavelength-dependency acquisition) allows all of the fluorescence to be acquired, thus allowing a high sensitivity of the system. This can be achieved without the cost and performance issues typically associated with the use of multi array detectors.
   b. The DLS data (signal intensity versus threshold wavelength) can be analyzed in new and powerful ways to determine the best setup for unmixing overlapping fluorochromes. This includes analyzing the slope and shape of signal/threshold-dependencies as well as scatter plots between several channels.
   c. The setup of the dynamic range of the system is much easier as compared with alternative sequential techniques.
   d. The signal strength in terms of photons per pixel can be very accurately determined by analyzing a DLS.
3. With respect to the production of 'pure' images free from spectral bleed through:
   a. The accuracy of the final images, either raw or unmixed is determined by the quality of the input images. The approach proposed here has great flexibility to allow the setup of optimal separating spectral division and does so with no sacrifice in terms of light efficiency. This will lead to a higher quality of the final image than the current alternatives.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

FIGS. 1 to 4 describe embodiments of a lasing scanner microscope suitable for carrying out the inventive method. Elements common to all embodiments are described in detail in connection with FIG. 1 only. However, they are present in all embodiments.

Figure 1:
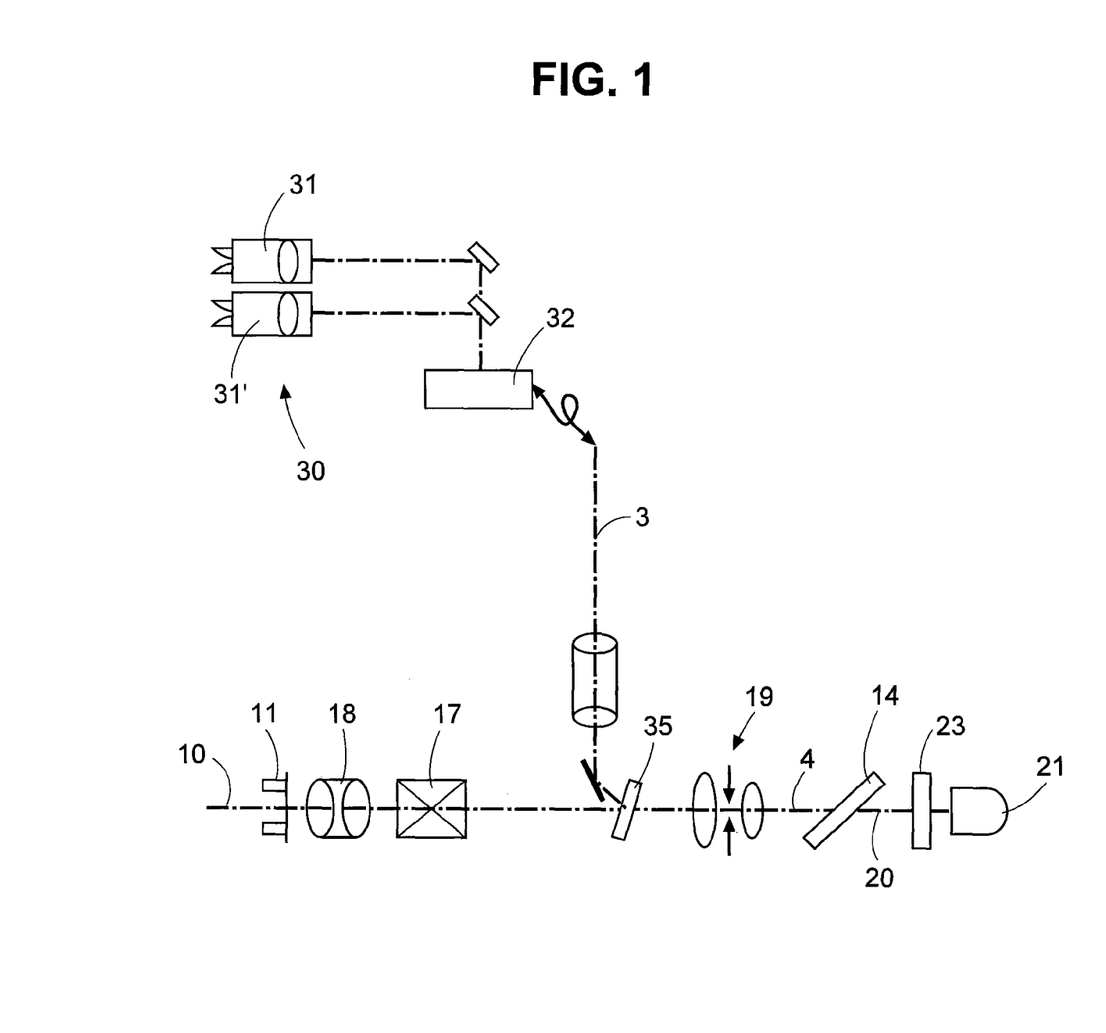
FIG. 1 shows a first embodiment of a laser scanning microscope suitable for carrying out the inventive method, which microscope is provided with a variable threshold beam splitter in the detection beam path and with a single detection channel.

The embodiment of FIG. 1 has a light source 30 comprising two lasers, namely a 555 nm laser 31 and a 488 nm laser 31'. Both lasers 31 and 31' are coupled via an AOTF 32 into an illuminating beam path 3. The microscope furthermore comprises a main beam splitter 35 constituted by a 488/561 notched main beam splitter, which directs the illuminating beam path 3 into the optical axis 10 of the microscope and ultimately on the sample which is not shown in the figures.

Between the main beam splitter 35 and a microscope connector 11 which serves for connecting a microscope optics, a sample stage etc., there is located a scanner 17 and a scan objective 18 of the microscope.

A detection beam path 4, originating at the sample, passes through the scan objective 18, the scanner 17 and the main beam splitter 35 to a pinhole optics 19, which allows to carry out confocal microscopy.

In the detection beam path 4, on the side of the main beam splitter 35 which is remote from the sample, there is an adjustable beam splitter 14, which is provided with an adjustable threshold wavelength between reflection and transmission. The beam splitter 14 can be a low-pass or a high-pass filter. It is formed by a color gradient filter having a varying threshold wavelength across its surface, so that the threshold wavelength within the detection beam path 4 can be set by changing the spatial position of the beam splitter 14 within the detection beam path 4.

Light passing through the beam splitter 14 enters a detection channel 20 and reaches detector 21. In the embodiment of FIG. 1, there is only one detection channel 20 (i.e., only one detector 21) and light reflected by the beam splitter 14 is lost.

Between the adjustable beam splitter 14 and the detector 21, there is provided an optional additional filter 23 which is designed as a filter wheel.

Figure 2:
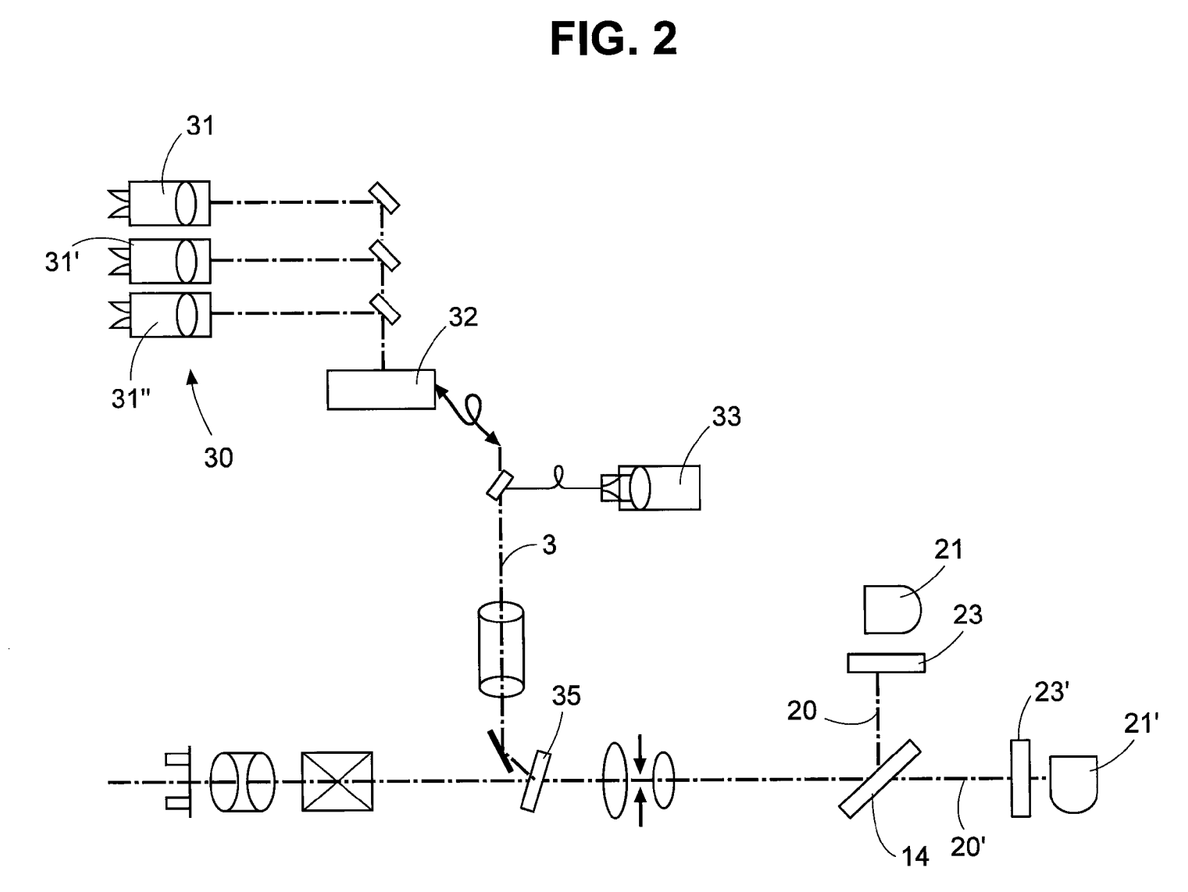
FIG. 2 shows a second embodiment of a laser scanning microscope suitable for carrying out the inventive method, which microscope is provided with a variable threshold beam splitter in the detection beam path and with two detection channels.

Another embodiment of a microscope suitable for use in connection with the inventive method is shown in FIG. 2. In contrast to FIG. 1, which shows a system with one detection channel, FIG. 2 shows a system with two detection channels. In case of the embodiment of FIG. 2, light reflected by the adjustable beam splitter 14 is led to a first detection channel 20 and to a first detector 21. Light passing through the adjustable beam splitter 14 is led to a second detection channel 20' with a second detector 21'. In both detection channels 20, 20', an optional additional filter 23, 23' is provided, which might be designed as a filter wheel.

Moreover, the light source 30 of the embodiment of FIG. 2 has more lasers as compared with the embodiment of FIG. 1. According to the embodiment of FIG. 2, there are three lasers, a 635 nm laser 31, a 555 nm laser 31', and a 488 nm laser 31", which are coupled via an AOTF 32 into the illuminating beam path 3. Moreover, there is a third 405 nm laser 33, which is coupled into the illuminating beam path 3 between the AOTF 32 and the main beam splitter 35, the latter being designed as a 405/488/555/635 notch beam splitter.

Figure 3:
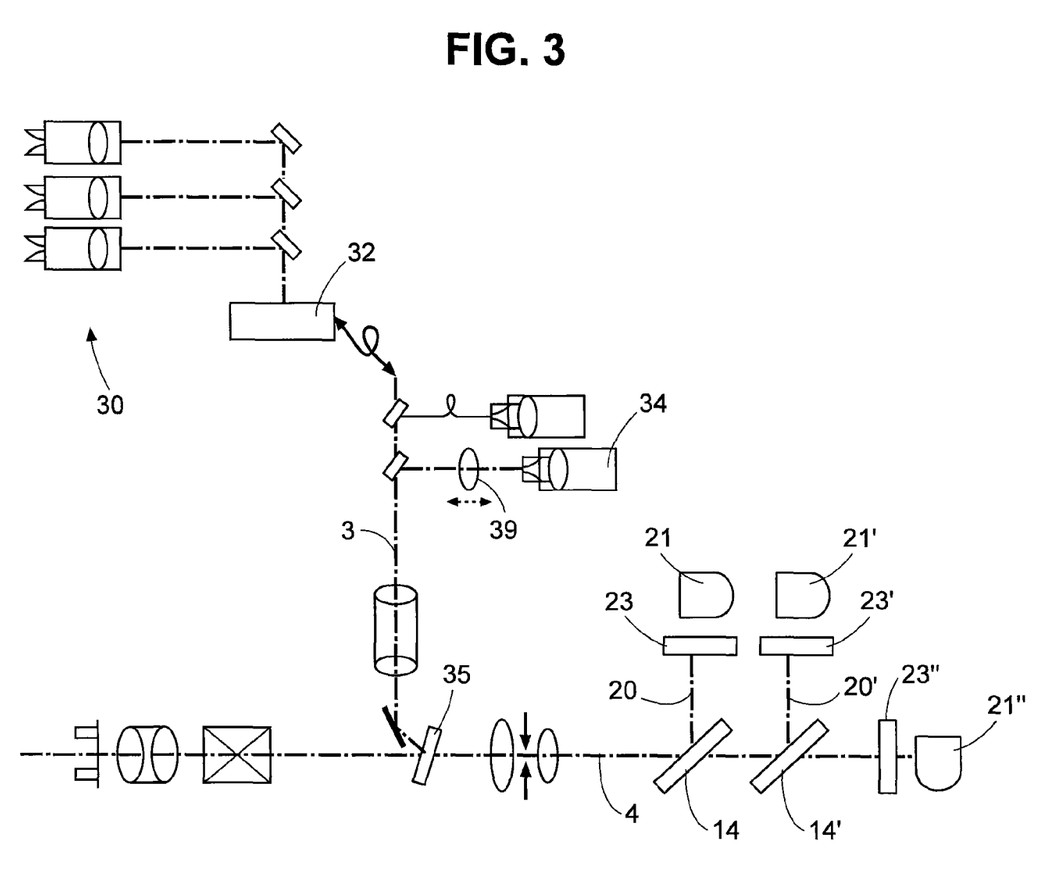
FIG. 3 shows a third embodiment of a laser scanning microscope suitable for carrying out the inventive method, which microscope is provided with two variable threshold beam splitters in the detection beam path and with three detection channels.

Whilst FIGS. 1 and 2 show one channel and two channel systems using a single adjustable beam splitter 14 to determine emission wavelength, the embodiment shown in FIG. 3 shows a three channel system using two adjustable beam splitters to determine emission wavelength.

In case of the embodiment of FIG. 3, there are two beam splitters 14 and 14' in succession in the detection beam path 4. Light reflected from the first beam splitter 14 goes into a first detection channel 20 and falls on a first detector 21. Emission light passing through the first beam splitter 14 falls on the second adjustable beam splitter 14'. Light reflected by this second beam splitter 14' goes into a second detection channel 20' and falls on a second detector 21'. Light passing both beam splitters 14 and 14' goes into a third detection channel 20" and falls on a third detector 21". In all detection channels 20, 20', 20", an additional filter 23, 23', 23" can be optionally provided. The light source 30 of the embodiment of FIG. 3 is the same as the light source of the embodiment of FIG. 2, with the exception that there is an additional TaiSap laser 34 having a variable collimation 39, which is coupled in the illuminating beam path 3 between the AOTF 32 and the main beam splitter 35. In case of the embodiment of FIG. 3, the main beam splitter 35 is a 405/488/555/635 notch and 700 short-pass beam splitter.

Figure 4:
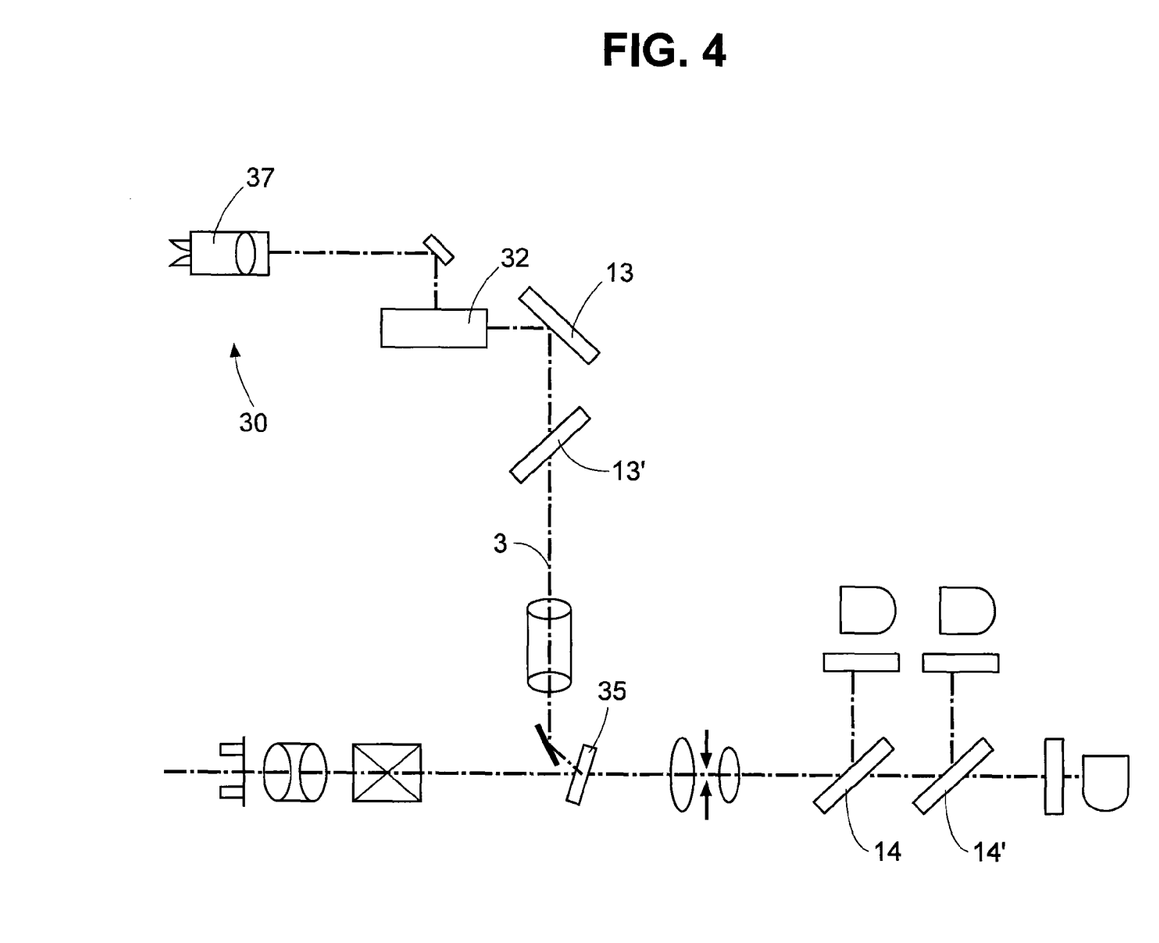
FIG. 4 shows a fourth embodiment of a laser scanning microscope suitable for carrying out the inventive method, which microscope is provided with two variable threshold beam splitters in the detection beam path and with three detection channels, and which microscope is moreover provided with a variable threshold beam splitters in the illuminating beam path.

An embodiment of a microscope having both spectrally tuneable excitation and emission is shown in FIG. 4. The embodiment of FIG. 4 is the same as the embodiment of FIG. 3, with the exception of the light source 30 and the illumination beam path 3. According to the embodiment of FIG. 4, the light source 30 has a broad wavelength source 37, for example a HBO or white light laser, which is coupled via an AOTF 32 into the illuminating beam path 3. For excitation wavelength selection, there are provided two adjustable beam splitters 13, 13' in the illumination beam path, between the AOTF 32 and the main beam splitter 35. These beam splitters 13, 13' can be configured as long-pass or short-pass filters. Preferably, one of the beam splitters 13, 13' is a long-pass filter and the other a short-pass filter.

Figure 5:
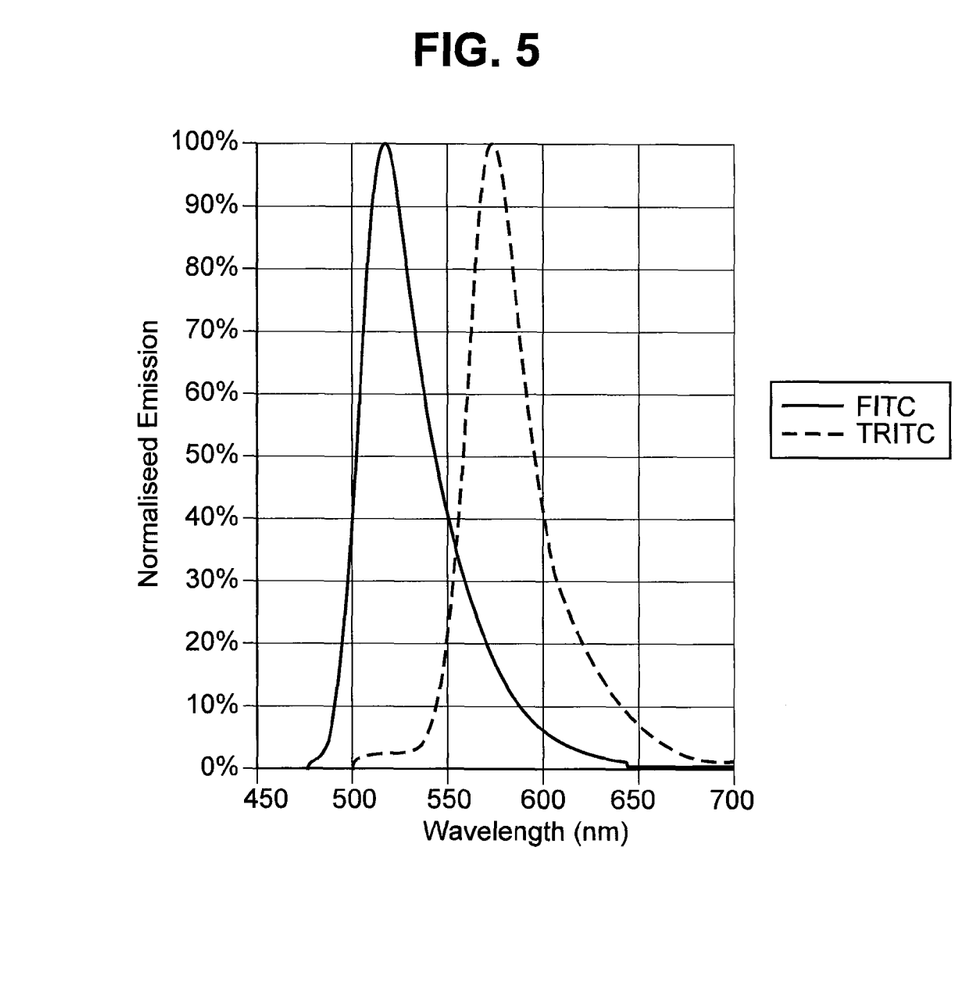
FIG. 5 shows a comparison of emission spectra of two sample fluorochromes (FITC and TRITC)

FIG. 5 shows a comparison of the emission spectra of two example fluorochromes, namely FITC and TRITC. Whilst FITC has an emission peak around 520 nm, TRITC has an emission peak around 570 nm.

Figure 6:
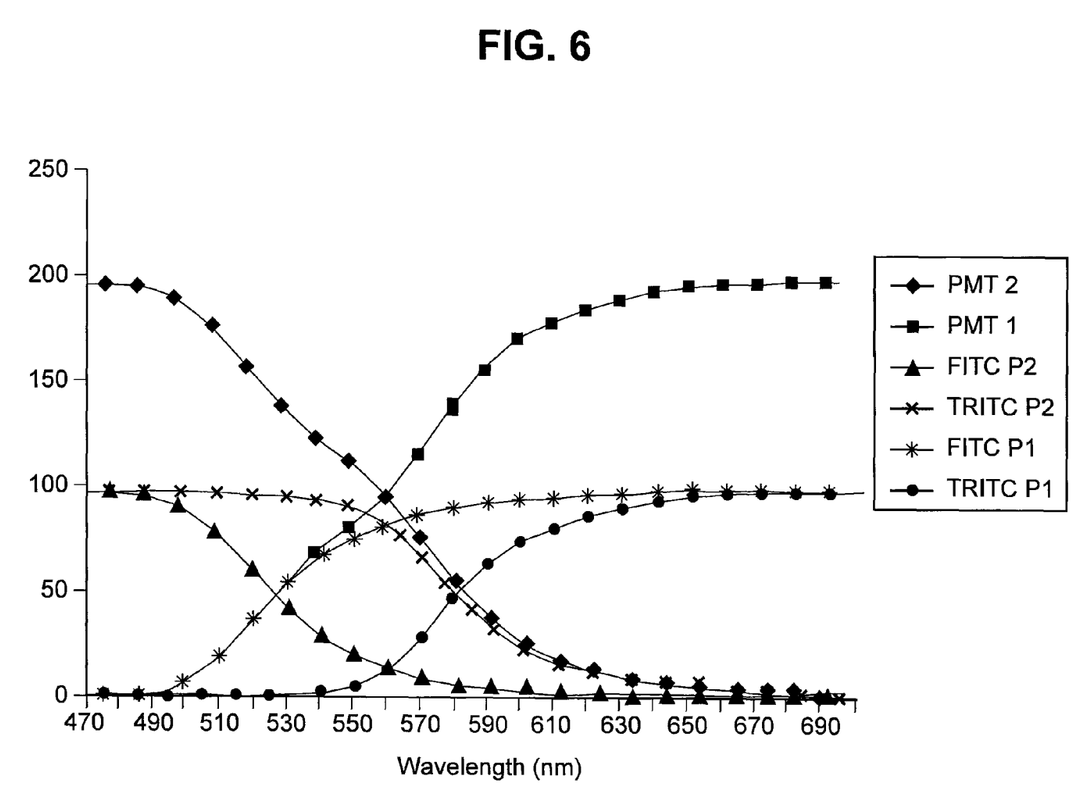
FIG. 6 shows an example of signal/threshold-dependencies in a two channel system for a sample containing FITC and TRITC fluorochromes.

FIG. 6 shows an example of signal/threshold-dependencies acquired in a two-channel system as for example shown in FIG. 2 and the accumulated sums per channel. In the example, the threshold wavelength of the adjustable beam splitter is changed in 10 nm steps, giving a two channel 10 nm differential emission series. The line FITC P1 shows the relative contribution of emission of FITC to the first channel. The line TRITC P1 shows the relative contribution of the TRITC emission to the first channel. In a similar way, the lines FITC P2 and TRITC P2 show the relative contributions of FITC and TRITC, respectively, to the second channel.

In channel one, both contributions FITC P1 and TRITC P1 sum up and give the signal/threshold-dependency of the first channel labelled PMT1. Equally, the contributions FITC P2 and TRITC P2 sum up in the second channel and give the signal/threshold-dependency PMT2 of the second channel.

Figure 7:
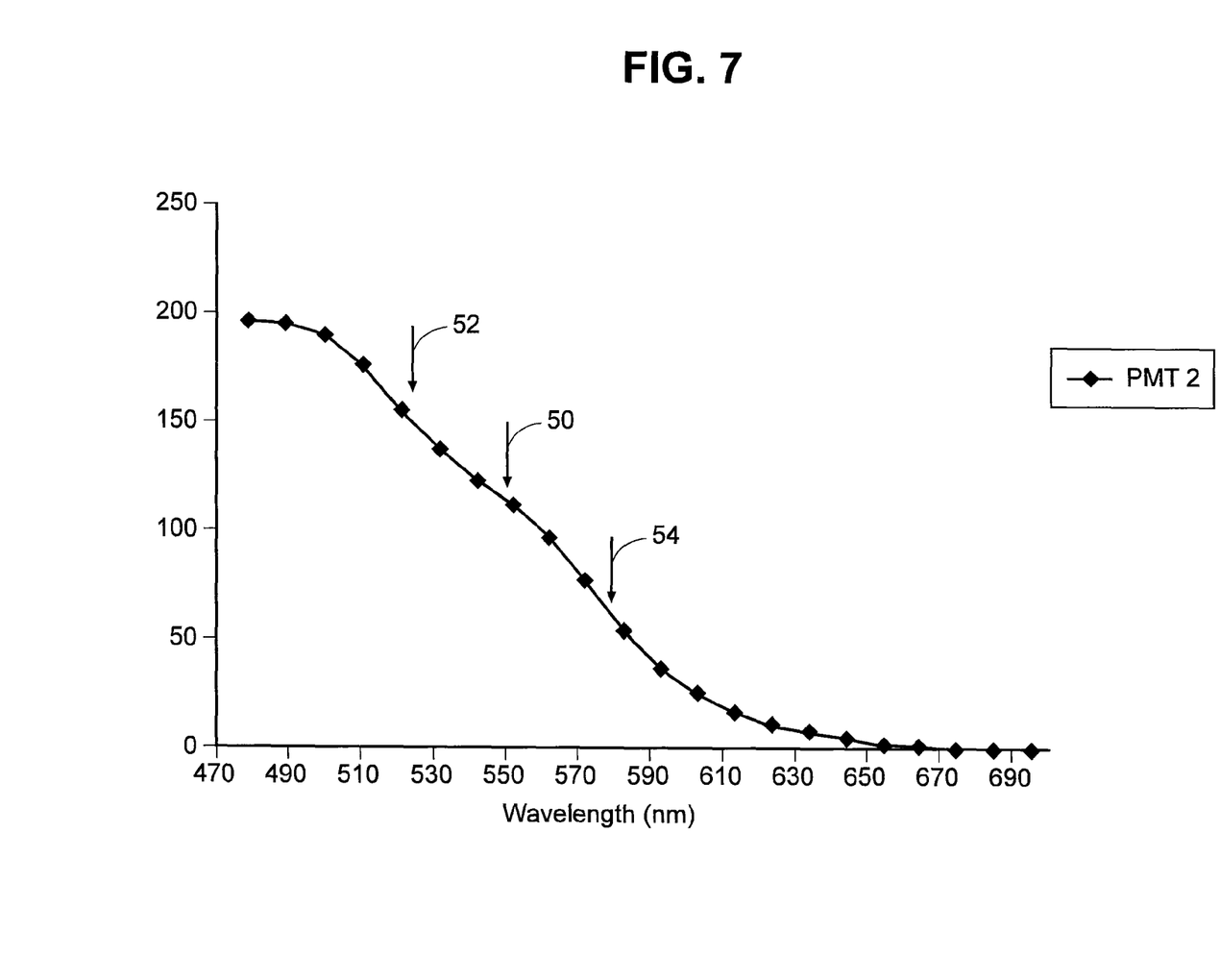
FIG. 7 shows the signal/threshold-dependency of the second channel of FIG. 6, to explain how spectral information can be gathered from the shape of the dependency.

The signal/threshold-dependency of the second channel, PMT2, of FIG. 6 (i.e., the accumulated totals for the emission series of FITC and TRITC) is shown in more detail in FIG. 7. In FIG. 7, the outermost arrows 52, 54 show the steepest descents of the graph, which correspond to the emission peaks of FITC and TRITC, respectively. The middle arrow 50 denotes the region where the absolute value of the gradient of the dependency has a local minimum (i.e., where the curve has a bump). The position of this middle arrow 50 represents the best point to set a spectral division means in order to acquire the spectral emission for the two fluorochromes with minimum effort required for subsequent unmixing of the images. In a case where the two fluorochromes have no overlap between the emission spectra, this part of the graph would be entirely flat.

Figure 8:
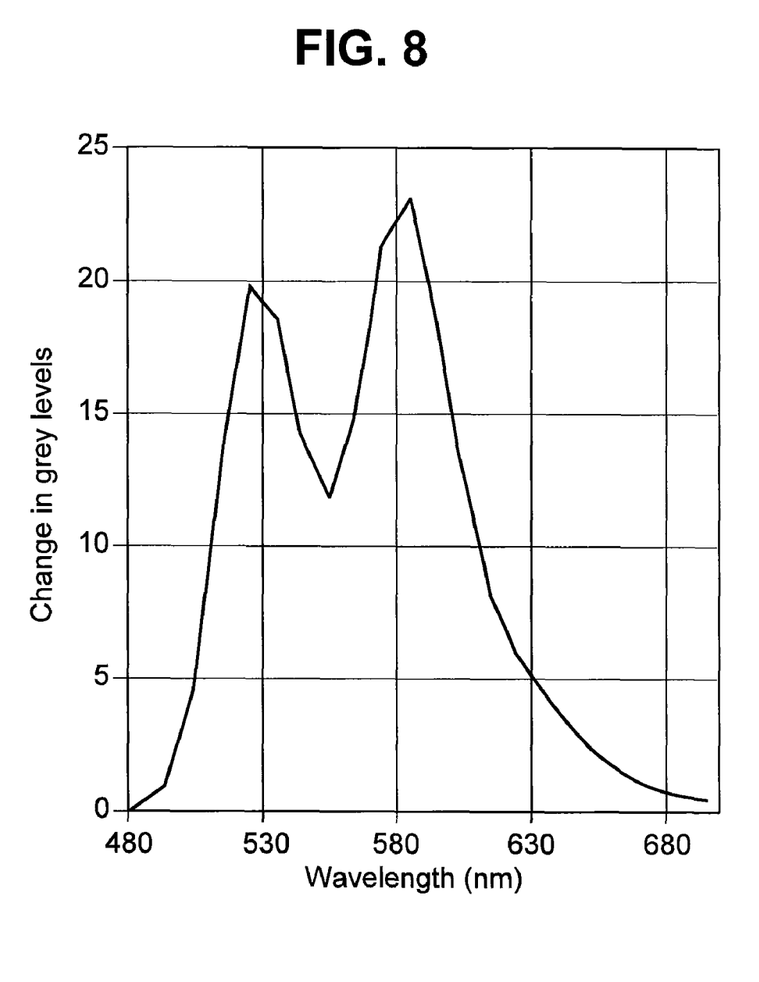
FIG. 8 shows a "traditional" signal versus wavelength spectrum derived from the signal/threshold-dependency of FIG. 7.

From the signal/threshold-dependency shown in FIG. 7, it is possible to back calculate to the "traditional" emission spectrum, showing the emission signal over the emission wavelength. The spectrum or the spectral curve resulting from such a "back calculating" of the dependency of FIG. 7 (i.e., from a differential spectral series) is shown in FIG. 8. FIG. 8 shows a curve equivalent to the summation of in the fluorochrome components in the measured pixel. It is calculated from the data shown in FIG. 7 by calculating the change in signal from one step to the next.

The example spectrum shown in FIG. 8 is for a pixel containing equal intensities of FITC and TRITC. It should be noted that the second peak is higher as the second peak is the peak emission wavelength for TRITC plus the bleed through of FITC, whereas the first peak is almost entirely just FITC. For a pixel containing just a single fluorochrome, the back calculated spectral series should have exactly the same shape as a spectral curve acquired on a "traditional" spectral system.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

What is claimed is:

1. A method for imaging a sample using a microscope, the method comprising:
   an illumination step in which a sample is illuminated with excitation light via an illuminating beam path; and
   a recording step in which light emitted from the sample is recorded via a detection beam path;
   wherein at least one adjustable beam splitter having an adjustable threshold wavelength between reflection and transmission is arranged in the detection beam path or/and in the illuminating beam path;
   wherein light emitted from the sample is detected in at least one detection channel;
   wherein, if the adjustable beam splitter is arranged in the detection beam path, the emitted light is split by the beam splitter and either emitted light passing through the beam splitter or light reflected by the beam splitter enters the detection channel;
   wherein, if the adjustable beam splitter is arranged in the illuminating beam path, a light spectrum of the light source is split by the beam splitter for varying the spectrum of the excitation;
   wherein the adjustable beam splitter is one of a low-pass filter and a high-pass filter;
   wherein, for at least one predetermined sample region, a signal intensity of light detected in the at least one detection channel is recorded for a plurality of threshold wavelengths set at the adjustable beam splitter to obtain a signal/threshold-dependency of the predetermined sample region; and
   wherein, from the signal/threshold-dependency or dependencies, at least one setting wavelength is determined, the setting wavelength representing a setup of the adjustable beam splitter for resolving fluorochromes with overlapping emission spectra, and the setting wavelength being a wavelength where emission lines of the fluorochromes show comparable intensities.

2. The method according to claim 1;
   wherein at least one fluorochrome on or in the sample is excited by the excitation light;
   wherein emission light is emitted by the fluorochrome; and
   wherein, for obtaining the signal/threshold-dependency, the adjustable beam splitter is set to a plurality of threshold wavelengths in a wavelength region where emission light of the fluorochrome occurs.

3. The method according to claim 1;
   wherein, by means of the adjustable beam splitter, the detection beam path is split into two detection channels; and
   wherein a signal/threshold-dependency is recorded for each of the two detection channels.

4. The method according to claim 3;
   wherein each of the two detection channels is provided with a first detector and a second detector; and
   wherein the threshold wavelength of the adjustable beam splitter is set to a first extreme wavelength so that the intensity at a first detector is at maximum, and then a range of the first detector is set; and
   wherein the threshold wavelength of the adjustable beam splitter is set to a second extreme wavelength so that the intensity at a second detector is at maximum, and then a range of the second detector is set.

5. The method according to claim 1;
   wherein signal/threshold-dependencies are recorded at a plurality of predetermined sample regions.

6. The method according to claim 1;
   wherein the threshold wavelength of the adjustable beam splitter is changed once a pixel, a line, a frame, or a z-stack has been scanned.

7. The method according to claim 1;
   wherein, from the signal/threshold-dependency, at least one setting wavelength is determined, the setting wavelength representing the best setup of a spectral division means for resolving fluorochromes with overlapping emission spectra.

8. The method according to claim 7;
wherein the setting wavelength is determined by analyzing the slope of the signal/threshold-dependency or dependencies.

9. The method according claim 7;
wherein threshold wavelength-dependent scatter plots, using the intensities of pixels in the two channels as its two axes, are generated from the signal/threshold-dependencies; and
wherein the setting wavelength is determined by analyzing the wavelength-dependent scatter plots.

10. The method according to claim 7;
wherein, subsequent to the determination of the setting wavelength, the adjustable beam splitter is set to the setting wavelength; and
wherein subsequently, with a fixed setting of the beam splitter at the setting wavelength, the sample or another sample is imaged.

11. The method according to claim 1;
wherein, from the signal/threshold-dependency, at least one spectrum of emission light emitted from the sample versus the wavelength of the emission light is calculated.

12. The method according to claim 1;
wherein there is at least one additional filter in the detection beam path in order to increase performance of a detector, located in the detection channel, in a threshold wavelength region to be studied.

13. The method according to claim 1;
wherein, based on an information of a detector response, a detector sensitivity of at least one detector of the detection beam path is changed as the threshold wavelength of the adjustable beam splitter is changed.

14. The method according to claim 1;
wherein the threshold wavelength of the adjustable beam splitter is changed in steps; and
wherein the size of the steps is changed based on the current threshold wavelength.

15. The method according to claim 14;
wherein the size of the steps is changed based on information obtained from a graphical representation of the signal/threshold-dependency; and
wherein the size of the steps is chosen such that the density of the steps per wavelength interval increases with the absolute value of the slope of the graphical representation of the signal/threshold-dependency.

16. The method according to claim 15;
wherein the signal/threshold-dependency used for determining the size of the steps is acquired by a measurement with reduced intensity of excitation light.

17. The method according to claim 1;
wherein, by means of the at least one adjustable beam splitter, the detection beam path is split into a plurality of detection channels;
wherein a signal/threshold-dependency is recorded for each of the detection channels;
wherein, from the signal/wavelength-dependencies of all channels, signal values present at a common threshold wavelength are extracted;
wherein the signal values present at the common threshold wavelength are added to give a summed signal value at the common threshold wavelength; and
wherein the summed signal value is used as a measure of signal strength.

18. The method according to claim 17;
wherein summed signal values are determined for a plurality of common threshold wavelengths; and
wherein the summed signal values are averaged to obtain a measure of signal strength with reduced relative shot noise.

19. A microscope being configured to automatically carry out the method according to claim 1.

20. The microscope according to claim 19;
wherein the microscope is a scanning microscope.

21. A data storage carrier on which a program for driving a control unit of a scanning microscope is stored;
wherein the program enables the operation of the microscope according to the method of claim 1.

* * * * *